(12) United States Patent
Uthgenannt et al.

(10) Patent No.: US 10,568,742 B2
(45) Date of Patent: Feb. 25, 2020

(54) TIBIAL INSERT

(71) Applicant: Zimmer, Inc., Warsaw, IN (US)

(72) Inventors: Brian A. Uthgenannt, Cricklade (GB); Jay Kendall, Ft. Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 141 days.

(21) Appl. No.: 15/831,828

(22) Filed: Dec. 5, 2017

(65) Prior Publication Data

US 2018/0153700 A1 Jun. 7, 2018

Related U.S. Application Data

(60) Provisional application No. 62/430,533, filed on Dec. 6, 2016.

(51) Int. Cl.
*A61F 2/38* (2006.01)
*A61F 2/30* (2006.01)

(52) U.S. Cl.
CPC .... *A61F 2/389* (2013.01); *A61F 2002/30329* (2013.01); *A61F 2002/30604* (2013.01); *A61F 2220/0025* (2013.01)

(58) Field of Classification Search
CPC .......... A61F 2/38; A61F 2/3868; A61F 2/389; A61F 2/3886; A61F 2002/30387
See application file for complete search history.

(56) References Cited

U.S. PATENT DOCUMENTS

| | | |
|---|---|---|
| 4,219,893 A | 9/1980 | Noiles |
| 6,660,039 B1 | 12/2003 | Evans et al. |
| 2003/0009232 A1* | 1/2003 | Metzger ................ A61F 2/3868 623/20.29 |
| 2004/0204765 A1 | 10/2004 | Fenning et al. |
| 2011/0196495 A1* | 8/2011 | Hunt ........................ A61F 2/28 623/17.16 |

FOREIGN PATENT DOCUMENTS

| | | |
|---|---|---|
| CN | 110022798 A | 7/2019 |
| WO | 2018106649 A1 | 6/2018 |

OTHER PUBLICATIONS

"International Application Serial No. PCT/US2017/064635, International Search Report dated Feb. 6, 2018", 5 pgs.
"International Application Serial No. PCT/US2017/064635, Written Opinion dated Feb. 6, 2018", 6 pgs.

* cited by examiner

*Primary Examiner* — Brian A Dukert
(74) *Attorney, Agent, or Firm* — Schwegman Lundberg & Woessner, P.A.

(57) ABSTRACT

Systems and apparatuses including a tibial insert for replacement of a knee joint of a patient are disclosed. The insert can comprise a proximal surface configured to interface with a bearing, a post and a distal surface. The post can extend from the proximal surface and can be configured to be received in a recess in the bearing. The bearing can be configured to pivot about the post to move relative to the proximal surface. The distal surface can be spaced from the proximal surface and can be configured to interface with a tibial baseplate. The distal surface can be configured with a connection mechanism to connect with the tibial baseplate.

19 Claims, 8 Drawing Sheets

TIBIAL INSERT

CLAIM OF PRIORITY

This application claims the benefit of priority to U.S. Provisional Application Ser. No. 62/430,533, filed on Dec. 6, 2016, which is incorporated herein by reference in its entirety.

FIELD

The present subject matter relates to orthopedic procedures and, more particularly, to inserts used with tibial baseplates and bearings in knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components, a replacement knee arthroplasty and a partial knee arthroplasty, where one damaged compartment of the knee is repaired with prosthetic components.

Overview

The present inventors recognize, among other things, an opportunity for facilitating rapid and convenient conversion from a fixed bearing knee prosthesis (where the bearing is fixed save for micro-motion relative to the tibial baseplate) to a mobile bearing knee prosthesis (where the bearing is rotatable or otherwise moveable relative to the tibial baseplate). More particularly, the present inventors have recognized that an insert can be configured to affix to the tibial baseplate using a connection mechanism that replicates those used on a distal portion of a fixed bearing. A proximal portion of the insert can be configured with a rotation post extending therefrom. The rotation post can be received in a recess in the bearing. The bearing can be configured to pivot about the post to move relative to the tibial baseplate and the insert. In this manner, the insert, bearing and tibial baseplate can comprise a mobile bearing knee prosthesis.

The present inventors have also recognized that surgical complexity can be reduced by providing a system where the tibial baseplate and insert do not need to be removed once implanted if wear on the bearing requires replacement and/or a different bearing design and femoral component is desired. For example, the system can have a plurality of bearings each of the plurality of bearings can have a different construction from one another. Each can be designed to work with different knee systems. For example, each of the plurality of bearings can be configured to articulate with a femoral implant of differing construction. Surgical complexity can also be reduced in that a fixed bearing prosthesis can be created (again) by simply fastening or otherwise affixing the bearing to the insert in some examples.

As used herein, "micro-motion" refers to the small motions that may exist between knee prosthesis assemblies, such as between the insert and the tibial baseplate respectively, upon application of force. Such small motions may occur as a result of material deformation in one or both of the interacting components, or may result from slight spaces or clearances therebetween, for example. Micro-motion is distinguished from "mobile" bearing applications, which experience relatively larger motions as the bearing articulates with respect to a tibial baseplate and insert (such as by sliding or rotating) along a desired motion path over the insert.

As used herein, "fixed" bearing applications are an assembly in which a bearing is seated atop the insert and/or tibial baseplate in a final, locked position. In this affixed position, lift-off of the bearing from the insert and/or tibial baseplate as well as transverse movement of the bearing component relative to the tibial tray is prevented (save for micro-motion) during natural articulation of the knee. While some micro-motion may exist between the bearing, the insert and/or tibial baseplate in a fixed bearing arrangement, no such motion occurs by design along any designated path.

Typically, bearings used in fixed bearing applications can have a connection mechanism that is employed to fix the bearing to the tibial baseplate, thereby creating the fixed bearing knee prosthesis. In the disclosed examples, the insert can be provided with the connection mechanism that is employed to connect the insert to the tibial baseplate. However, the disclosed interaction between the bearing and the insert can be that of a mobile bearing application as the bearing articulates with respect to the insert (such as by sliding or rotating) along a desired motion path over the insert.

According to some examples, the connection mechanism can include a dovetail boss on the tibial baseplate cooperating with a corresponding notch on a insert, a peripheral rail of the tibial baseplate cooperating with a corresponding recessed portion of the insert, a pair of anterior wedges projecting from an anterior edge of the insert that cooperate with an undercut within an anterior peripheral rail of the tibial baseplate, a bond or over-mold of the insert to the tibial baseplate, or any combination of these features.

To further illustrate the apparatuses and methods disclosed herein, the following non-limiting examples are provided:

Example 1 is a tibial insert for replacement of a knee joint of a patient, the insert can comprise a proximal surface, a post and a distal surface. The proximal surface can be configured to interface with a bearing. The post can extend from the proximal surface and can be configured to be received in a recess in the bearing. The bearing can be configured to pivot about the post to move relative to the proximal surface. The distal surface can be spaced from the proximal surface and can be configured to interface with a tibial baseplate. The distal surface can be configured with a connection mechanism to connect with the tibial baseplate.

In Example 2, the subject matter of Example 1 optionally can include a stop extending from the proximal surface and configured to limit movement of the bearing relative to the insert about the post.

In Example 3, the subject matter of Example 2 optionally can include the stop is configured with a patellar relief recess therein.

In Example 4, the subject matter of any one or more of Examples 1-3 optionally can include the proximal surface is substantially planar.

In Example 5, the subject matter of any one or more of Examples 1-4 optionally can include the insert has a differing thickness between the proximal surface and the distal surface as measured at one or both of a medial edge relative to a lateral edge and an anterior edge relative to a posterior edge.

In Example 6, the subject matter of any one or more of Examples 1-5 optionally can include the insert includes an internal lattice to reinforce the insert.

In Example 7, the subject matter of any one or more of Examples 1-6 optionally can include the connection mechanism comprises a dovetail configured to mate with a corresponding second dovetail provided by the tibial baseplate.

In Example 8, the subject matter of any one or more of Examples 1-7 optionally can include a recess in the post and the post configured with a connection feature within the recess to facilitate lockdown of the bearing to the inert.

In Example 9, the subject matter of any one or more of Examples 1-8 optionally can include the bearing comprises one of a medial congruent design, an ultra-congruent design, a posterior constrained design and a posterior constrained revision design.

Example 10 is a system for replacement of a knee joint of a patient, the system can comprise a tibial baseplate, one or more bearings, and an insert. The tibial baseplate can be configured to couple to a resected proximal surface of a tibia. The insert can be disposable between the one or more bearings and the tibial baseplate. The insert can comprise a proximal surface, a post and a distal surface. The proximal surface configured to interface with the one or more bearings. The post can extend from the proximal surface and can be configured to be received in a recess in each of the one or more bearings. Each of the one or more bearings can be configured to pivot about the post to move relative to the proximal surface. The distal surface can be spaced from the proximal surface and can be configured to interface with the tibial baseplate, wherein the distal surface is configured with a connection mechanism to connect with the tibial baseplate.

In Example 11, the subject matter of Example 10 optionally can include the one or more bearings comprises a plurality of bearings each of the plurality of bearings have a different construction and are configured to simulate a bearing from a different knee system, and wherein each of the plurality of bearings are configured to articulate with a femoral implant of a different construction.

In Example 12, the subject matter of any one or more of Examples 10-11 optionally can include the one or more bearings are configured to be substitutable for one another on the insert without removal of the tibial baseplate and the insert from the knee joint of the patient.

In Example 13, the subject matter of any one or more of Examples 10-12 optionally can include the insert includes a stop extending from the proximal surface and configured to limit movement of the one or more bearings relative to the insert about the post.

In Example 14, the subject matter of Example 13 optionally can include the stop is configured with a patellar relief recess therein.

In Example 15, the subject matter of any one or more of Examples 10-14 optionally can include the proximal surface is substantially planar.

In Example 16, the subject matter of any one or more of Examples 10-15 optionally can include the insert has a differing thickness between the proximal surface and the distal surface as measured at one or both of a medial edge relative to a lateral edge and an anterior edge relative to a posterior edge.

In Example 17, the subject matter of any one or more of Examples 10-16 optionally can include the insert includes an internal lattice to reinforce the insert.

In Example 18, the subject matter of any one or more of Examples 10-17 optionally can include the connection mechanism comprises a dovetail configured to mate with a corresponding second dovetail provided by the tibial baseplate.

In Example 19, the subject matter of any one or more of Examples 10-18 optionally can include the one or more bearings comprises at least one of a medial congruent design, an ultra-congruent design, a posterior constrained design and a posterior constrained revision design.

Example 20 is a system for replacement of a knee joint of a patient, the system can comprise a tibial baseplate, an insert and a bearing. The tibial baseplate can be configured to couple to a resected proximal surface of a tibia. The insert can be configured to affix to the tibial baseplate. The insert can have a proximal surface and a post extending from the proximal surface. The bearing can be configured to receive the post therein. The bearing can be configured to pivot about the post to move relative to the proximal surface.

In Example 21, the subject matter of Example 20 optionally can include the bearing comprises a plurality of bearings each of the plurality of bearings have a different construction and are configured to simulate a bearing from a different knee system, and wherein each of the plurality of bearings are configured to articulate with a femoral implant of a different construction.

In Example 22, the subject matter of Example 21 optionally can include the plurality of bearings are configured to be substitutable for one another on the insert without removal of the tibial baseplate and the insert from the knee joint of the patient.

In Example 23, the apparatuses or method of any one or any combination of Examples 1-22 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to prostheses and systems that can be used in various knee replacement procedures including total knee (TKA) and revision knee replacement procedures, and other types of knee replacement procedures. The disclosed apparatuses can include a tibial baseplate, a bearing and an insert. According to some examples, the insert can be configured to affix to the tibial baseplate and can be configured with a rotation post extending from a proximal surface. The rotation post can be received in a recess in the bearing. The bearing can be configured to pivot about the post to move relative to the tibial baseplate and the insert. In this manner, the prosthesis assembly can comprise a mobile bearing knee prosthesis.

As used herein, "proximal" refers to a direction generally toward the torso of a patient, and "distal" refers to the opposite direction of proximal, i.e., away from the torso of a patient. As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior". Similarly, the terms "medial" and "lateral" should be given their generally understood anatomical interpretation. "Medial" refers to the opposite direction of "lateral".

Figure 1:
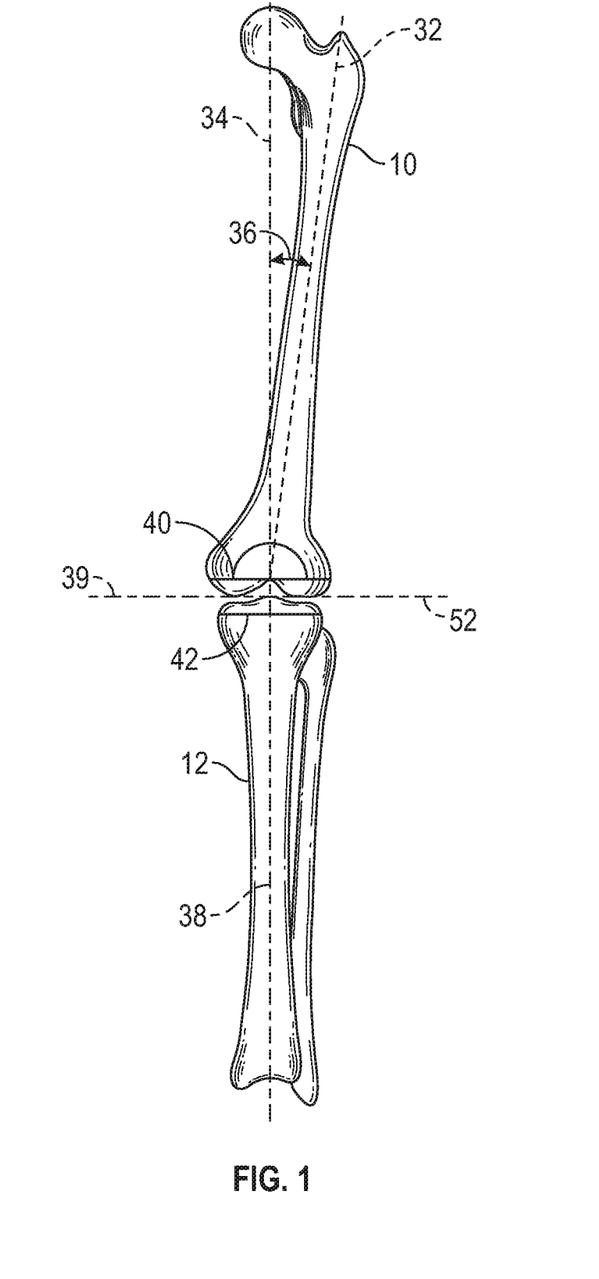
FIG. 1 is a front elevation view of a tibia and a femur showing axes of the knee joint according to example of the present application.

FIG. 1 illustrates a natural femur 10 and tibia 12 and illustrates several aspects of prosthesis orientation. FIG. 1 illustrates various axes of the lower limb in the frontal plane.

Axes can be defined for each segment of the lower limb. For example, the femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane. Likewise, the tibia 12 has a mechanical axis 38 coinciding generally with its intramedullary canal. The mechanical axis 38 of the tibia 12 runs from the center of the knee to the center of the ankle. The transverse axis, or joint line 38, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

The distal femoral cut is typically made perpendicular to the femoral axes 32, 34 in the sagittal plane. The proximal tibial resection is typically cut to match the natural posterior slope, or rotation, of the proximal tibia relative to the mechanical axes 34, 38. The amount of posterior to anterior slope (i.e. the change of resection 42 anterior to posterior relative to a reference line 52 perpendicular to the mechanical axes 34, 38 varies in the patient population but is on the order of 5° to 7°. Other cuts may be made depending on the components that are to be implanted.

Figure 2:
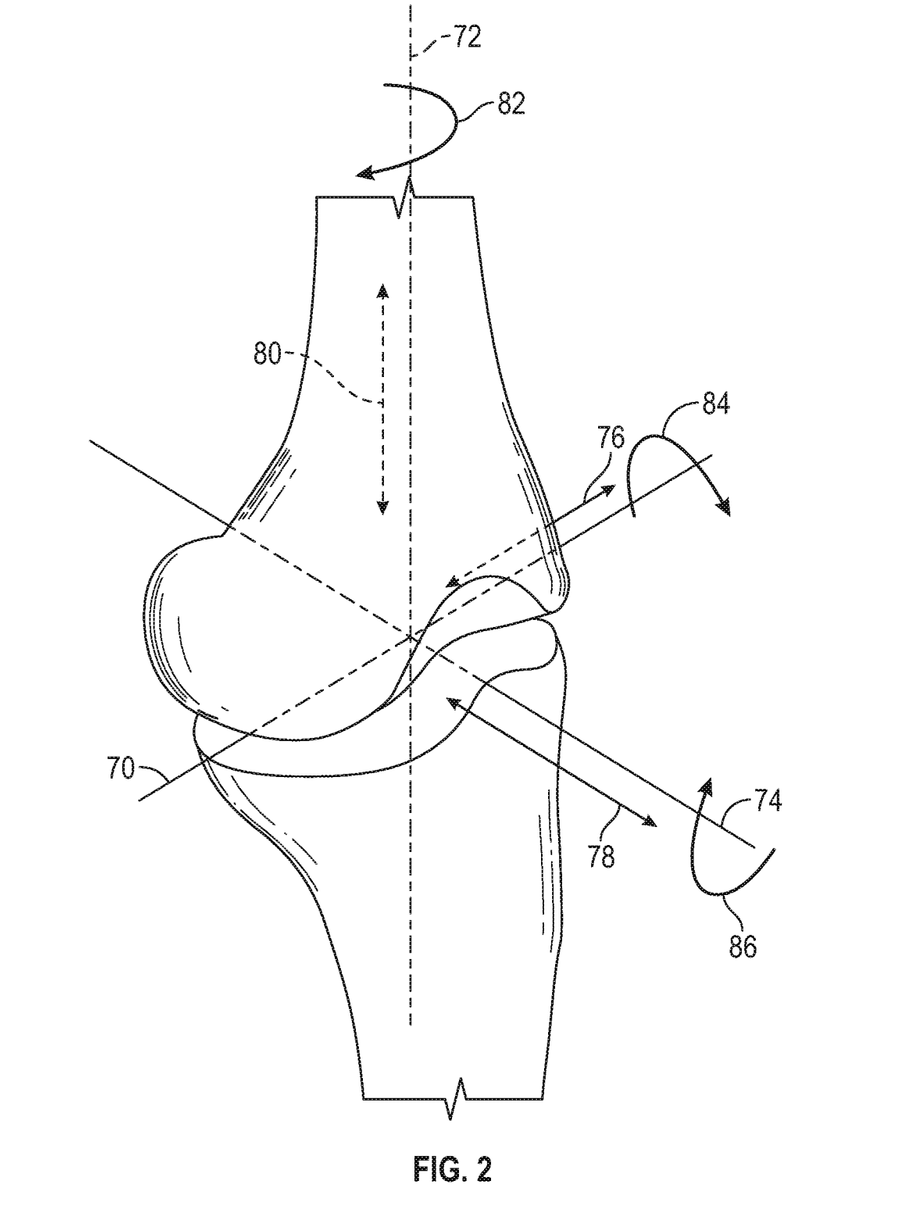
FIG. 2 is a perspective view of knee joint showing aspects of component positioning according to example of the present application.

FIG. 2 depicts six aspects of component positioning relative to a coordinate system in which the x-axis 70 corresponds approximately to the joint line 39, the z-axis 72 corresponds approximately to the mechanical axes 34 and 38, and the y-axis 74 is normal to the other two. Position along each of these axes is depicted by arrows. Position along the x, y, and z axes determines the medial/lateral (dx) 76, anterior/posterior (dy) 78, and proximal/distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

Figure 3A:
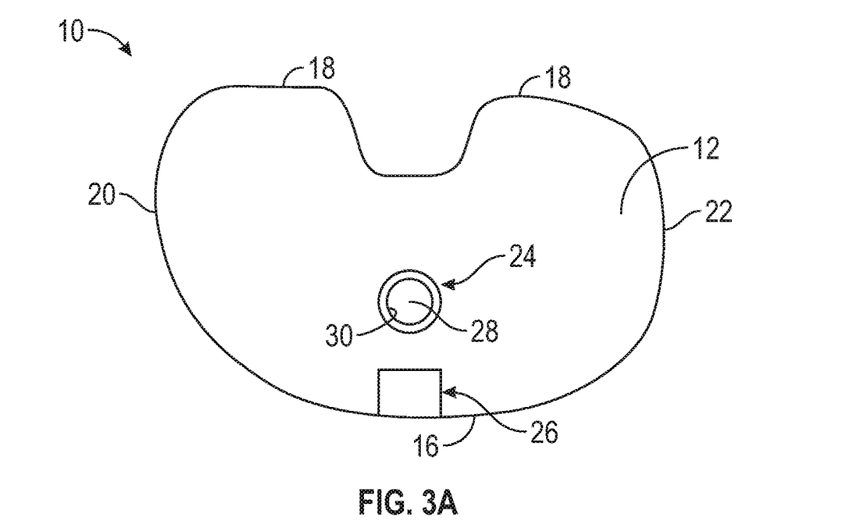
FIG. 3A is a plan view of a proximal side of an insert for a tibial baseplate according to example of the present application.
Figure 3B:
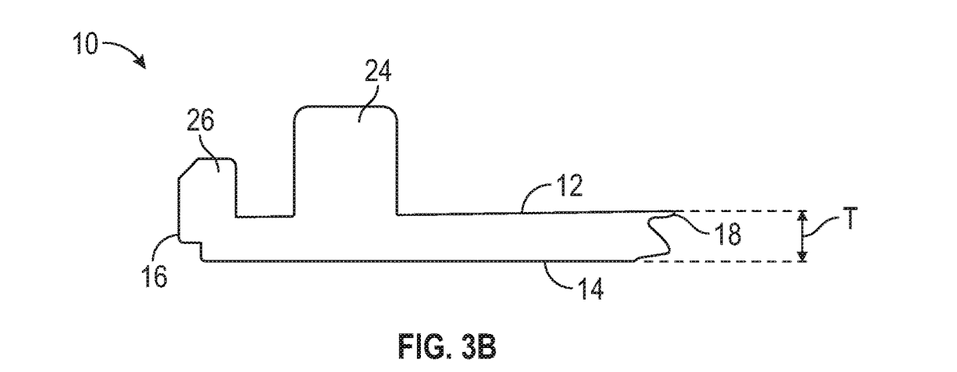
FIG. 3B is a plan view of a medial or lateral side of the insert according to example of the present application.
Figure 3C:
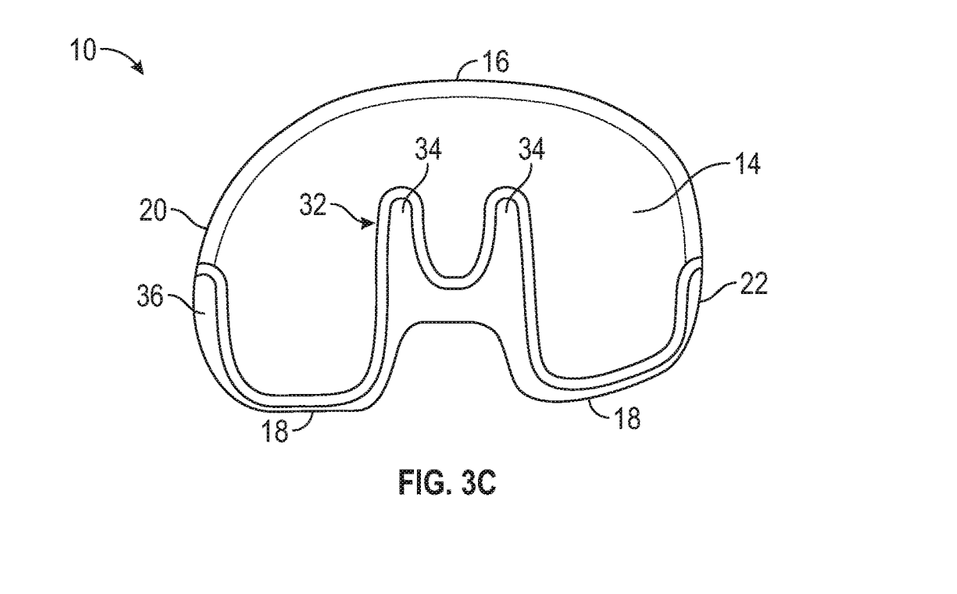
FIG. 3C is a plan view of a distal side of the insert according to example of the present application.

FIGS. 3A-3C show an insert 10 from various perspectives. FIG. 3A shows a top view of a proximal surface 12 of the insert 10. FIG. 3B shows the insert 10 from a medial or lateral side. FIG. 3C shows a distal surface 14 of the insert 10 opposing the proximal surface 12 (FIGS. 3A and 3B).

FIGS. 3A-3C variously show that the insert 10 can include an anterior edge 16, a posterior edge 18, a medial edge 20, a lateral edge 22, a post 24 and a stop 26. The post 24 can include a recess 28 as shown in FIG. 3A.

The proximal surface 12 can extend from the anterior edge 16 to the posterior edge 18 and from the medial edge 20 and the lateral edge 22. Similarly, the distal surface 14 can extend from the anterior edge 16 to the posterior edge 18 and from the medial edge 20 and the lateral edge 22. The proximal surface 12 can be opposed by the distal surface 14. The insert 10 can have a thickness T (shown in FIG. 3B) as measured from the proximal surface 12 to the distal surface 14. The thickness T can vary from example to example but can be about 4 mm according to one example.

According to the illustrated example, the proximal surface 12 can be substantially planar save for the post 24 and the stop 26. The post 24 can be centrally situated between the medial side and the lateral side of the insert 10 and can extend generally proximally from the proximal surface 12. According to further examples, the position of the post 24 can be varied any one or combination of medially, laterally, anteriorly or posteriorly so as to be biased relatively closer to one or more of the aforementioned edges 16, 18, 20 and 22. The position of the post 24 can be dictated by the desired kinematics for the knee joint. The post 24 can be cylindrical in shape and can have the recess 28 extending therein. The post 24 can be configured with a connection feature 30 (e.g., threading, key, snap-fit, or the like) within the recess 28 to facilitate lockdown of the bearing to the insert 10 with a fastener or other feature in some examples where a fixed bearing knee prosthesis is desired.

The stop 26 can be positioned anterior of the post 28 and can be positioned at and extend posterior of the anterior edge 16. The stop 26 can extend generally proximally from the proximal surface 12. The stop 26 can comprise a rotational stop to limit rotation of the bearing in cases of extreme flexion, extension or the like. The stop 26 may not be present in all examples of the insert or may not be used with all bearing designs.

The insert 10 can be constructed of various biocompatible materials. In some cases, the insert 10 can be a composite. The proximal surface 12 can be formed by a metal or alloy such as cobalt-chromium-molybdenum or titanium. The distal surface 14 can be formed by a polymer such as an ultra-high weight polyethylene or polyether ether ketone.

Figure 8:
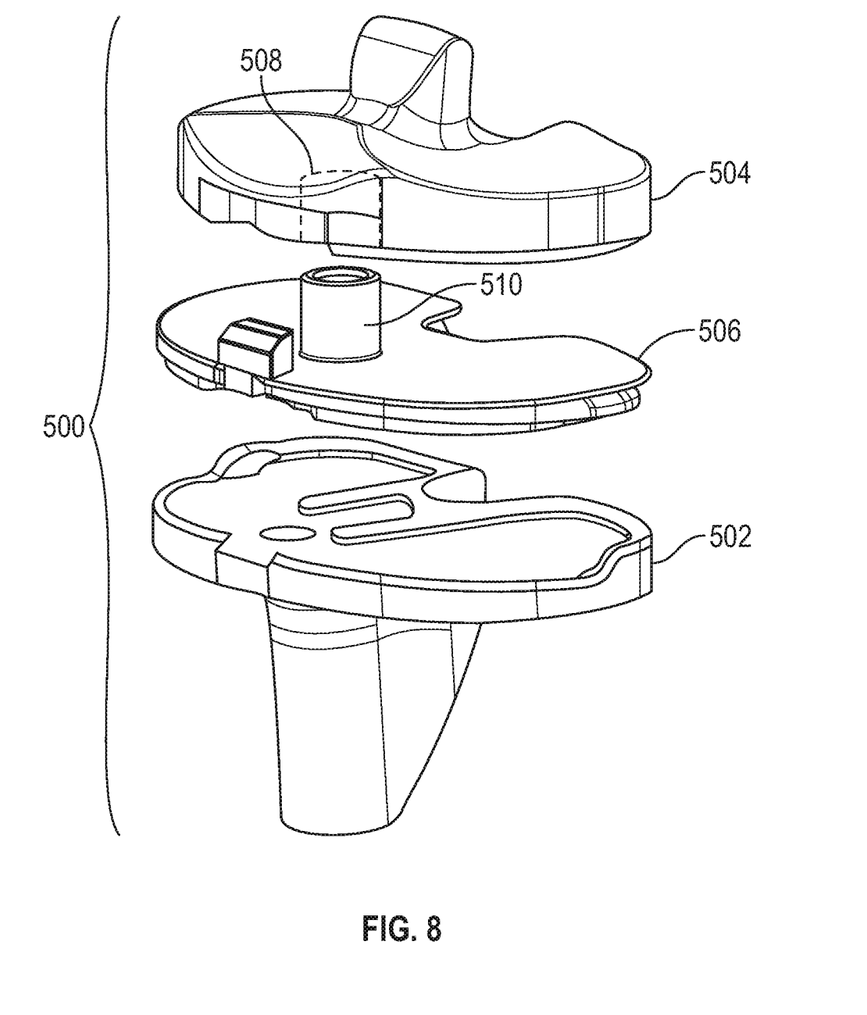
FIG. 8 is a perspective view of a system including one or more bearings, an insert and a tibial baseplate according to another example of the present application.
Figure 9A:
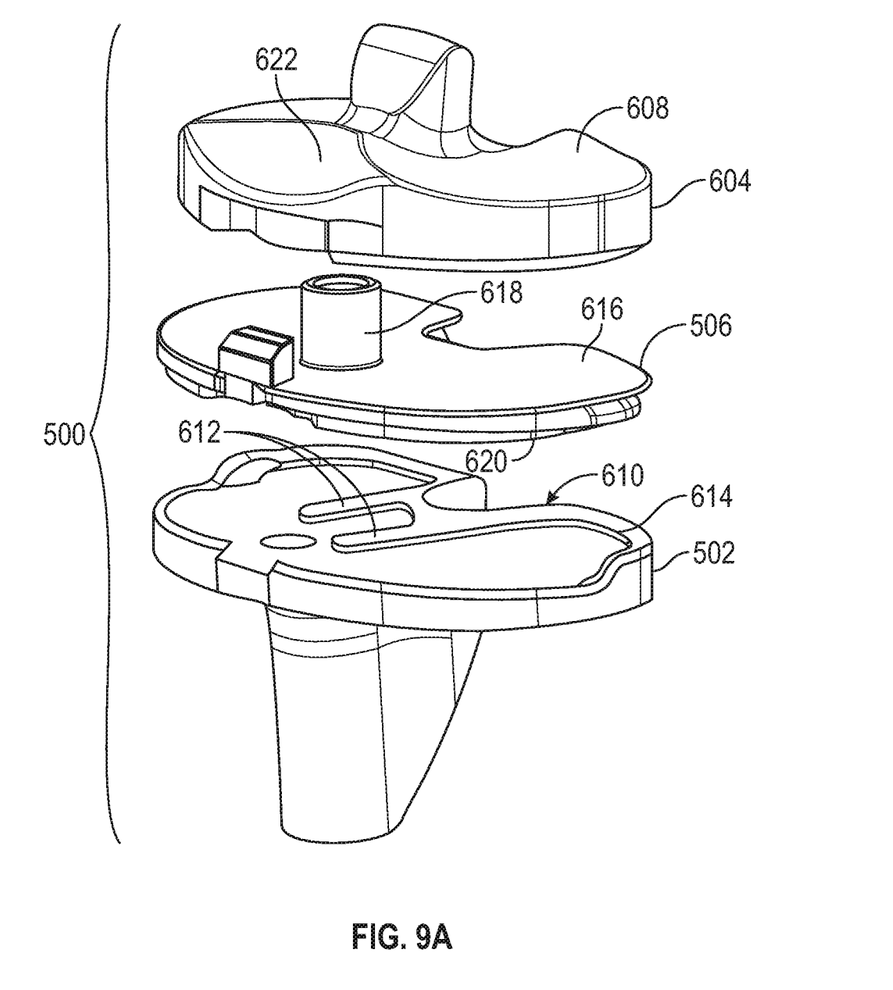
FIGS. 9A and 9B are perspective views of the system of FIG. 8 with a specific example of a posterior stabilized bearing having a construction of that of a bearing from Zimmer Biomet's Persona® Knee System according to an example of the present application.
Figure 9B:
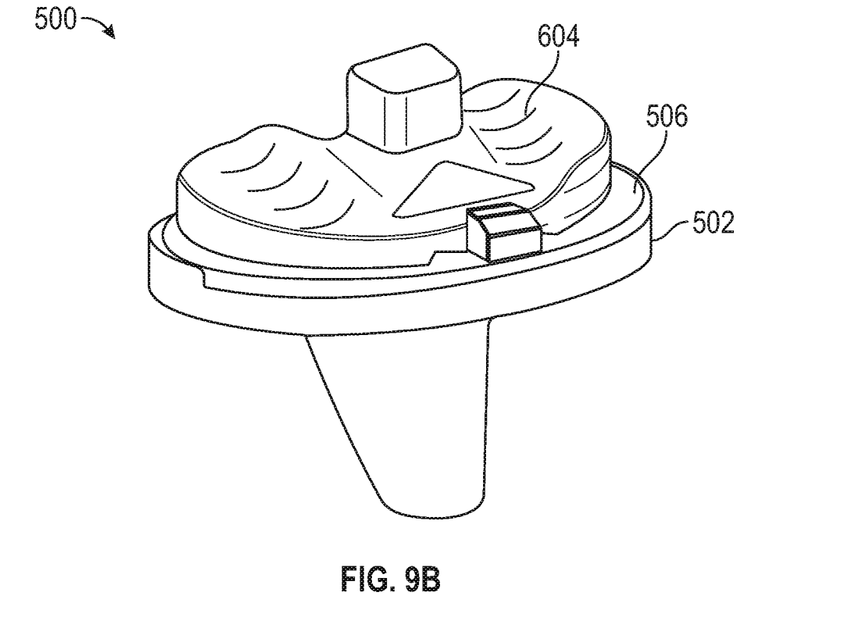

As shown in FIGS. 3B and 3C, the insert 10 can form a portion of a connection mechanism 32 that can also be shared with the tibial baseplate (FIGS. 8-9B). In the exemplary embodiment, the connection mechanism 32 can comprise a notch 34 having a double dovetail geometry configured to receive a double dovetail projection from the tibial baseplate. The insert 10 also can include a recessed portion 36 configured to receive a peripheral rail of the tibial baseplate. Further information regarding the notch 34 and recessed portion 36 can be found in U.S. Pat. No. 8,628,580, filed Jul. 22, 2011, the entire disclosure of which is incorporated herein by reference.

According to the example of FIGS. 3B-3C, the connection mechanism 32 of the insert 10 and indeed the shape and thickness of the insert 10 can be configured for use with a tibial baseplate from Zimmer Biomet's Persona® Knee System. Thus, the insert 10 can have the aforementioned notch 34 and recessed portion 36 and can be asymmetrically shaped such that a medial portion of the insert 10 is larger than the lateral portion. This asymmetric shape is configured to correspond to that of the tibial baseplate from Zimmer Biomet's Persona® Knee System. However, in other examples the insert 10 can be configured to connect to and correspond with other tibial baseplates from different commercialized or yet to be commercialized knee systems.

Figure 4A:
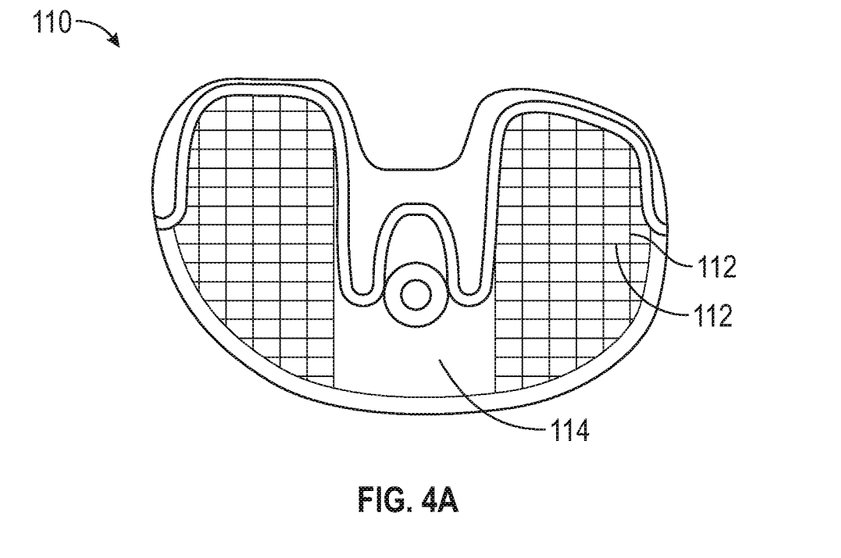
FIG. 4A is a plan view of a distal side of another example of the insert having a lattice reinforcement.
Figure 4B:
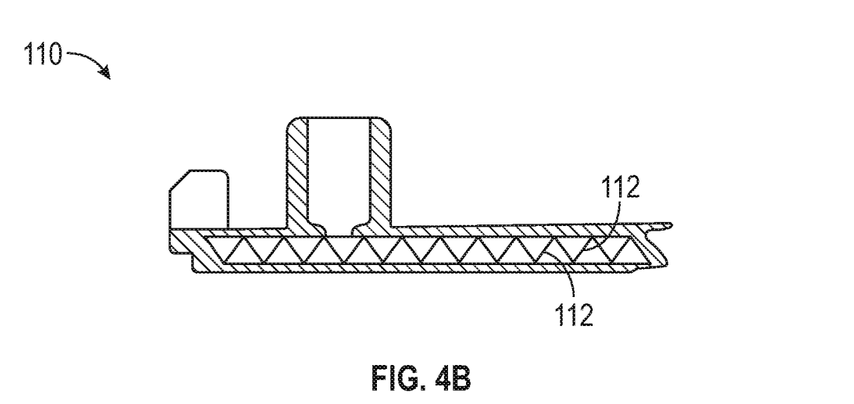
FIG. 4B is a sectional view of the insert with the lattice of FIG. 4A according to example of the present application.

FIGS. 4A and 4B show an insert 110 of similar construction to that of the insert 10. The insert 110 can include a lattice 112 for additional strength. The lattice 112 can be internal to the insert 110 (i.e. can be disposed under the surfaces thereof). As shown in FIG. 4A, the lattice 112 can be square shaped in a first plane. The lattice 112 can be joist or triangular shaped in a second plane as shown in FIG. 4B.

According to one example, the insert 110 can be a polymer over-mold throughout. The lattice 112 can be bonded or laser sintered to the distal surface 114 (partially shown in FIG. 4A) according to other examples.

Figure 5:
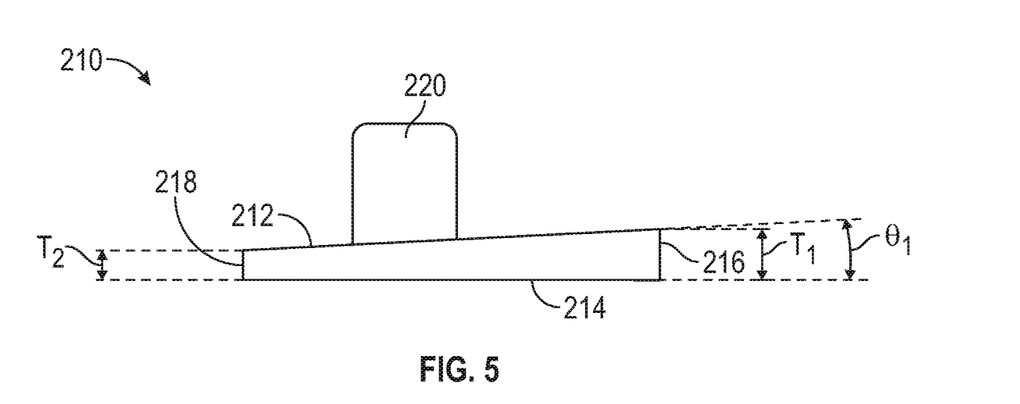
FIG. 5 is a plan view from a medial or lateral side of another example of the insert, the insert having an anterior-posterior differential thickness according to example of the present application.
Figure 6:
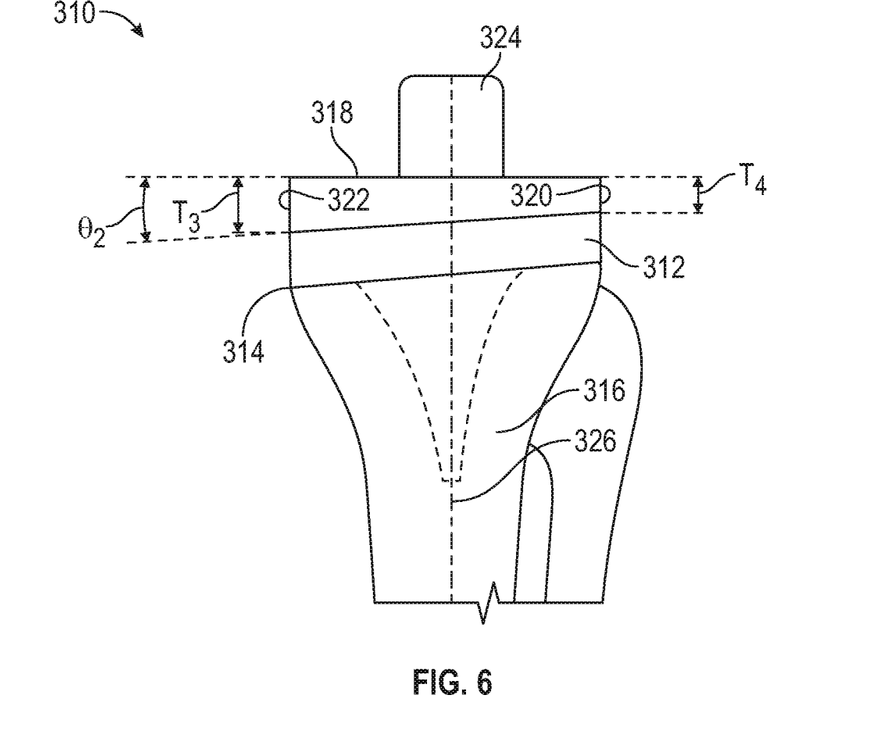
FIG. 6 is a plan view from an anterior side of a knee joint showing another example of the insert, the insert having a medial-lateral differential thickness according to example of the present application.

FIGS. 5 and 6 illustrate inserts 210 and 310, respectively. The inserts 210 and 310 can have a differing thicknesses between the proximal surface and the distal surface as measured at one or both of a medial edge relative to a lateral edge and an anterior edge relative to a posterior edge.

In particular, the insert 210 can include a proximal surface 212, a distal surface 214, an anterior edge 216 and a posterior edge 218. A thickness T1 of the insert 210 at the anterior edge 216 can differ from a thickness T2 at the posterior edge 218. This difference in thickness T1 relative to thickness T2 can create and angle $\theta 1$ as measured anterior-posterior relative to the distal surface 214 and the baseplate once the insert 210 is affixed thereto. Typically, the angle $\theta 1$ will be on the order of 0.1° to 3° but can be any angle as desired. Although shown with the anterior edge 216 having a greater thickness than the posterior edge 218, such arrangement can be reversed in some examples. The difference in difference in thickness T1 relative to thickness T2 can be used to change the posterior to anterior slope discussed in reference to FIG. 1. This adjustment can be done to achieve desired ligament balance and can be done either intra-operatively or post-operatively (in instances of a revision). In some instances, the difference in thickness T1 relative to thickness T2 can be used to correct a misalignment between the femoral prosthesis and the tibial baseplate. As shown in FIG. 5, a post 220 may or may not be angled by $\theta 1$ similar to the proximal surface 212. In some cases the post 220 can be aligned with the mechanical axis of the tibia in a manner similar to the insert 310 of FIG. 6.

FIG. 6 shows the insert 310 can be fixed to the baseplate 312, which in turn can be mounted to a resected proximal surface 314 of a tibia 316. As shown in FIG. 6, the insert 310 can have a proximal surface 318, a medial edge 320 and a lateral edge 322. A thickness T3 of the insert 310 at the lateral edge 322 can differ from a thickness T4 at the medial edge 320. This difference in thickness T3 relative to thickness T4 can create and angle $\theta 2$ as measured medial-lateral relative to the distal surface of the insert 310 and the baseplate 312. Although shown with the lateral edge 322 having a greater thickness than the medial edge 320, such arrangement can be reversed in some examples. Indeed, as should be evident from FIGS. 5 and 6, the insert can be given a varying thickness as desired and can have a varying thickness in multiple directions (e.g., anterior-posterior and medial-lateral) in some cases. The difference in the thickness T3 relative to thickness T4 can be used to correct or slightly adjust the varus/valgus angle of the resected proximal surface 314 of the tibia 316. As shown in FIG. 6, a post 324 may or may not be angled by $\theta 2$ similar to the proximal surface 314. For example, the post 324 can be aligned with the mechanical axis 326 of the tibia 316.

Figure 7:
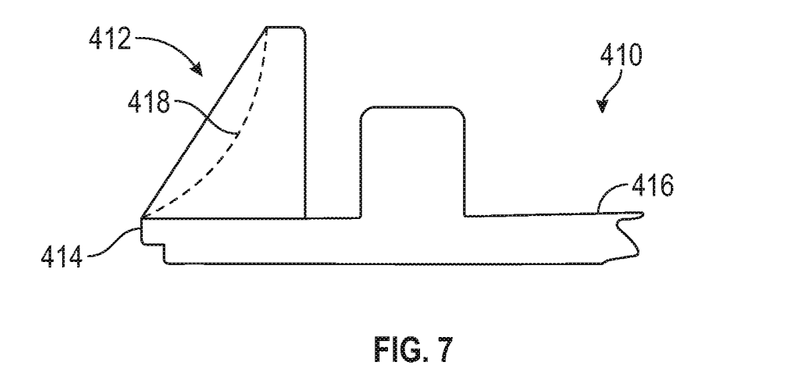
FIG. 7 is a plan view from a medial or lateral side of another example of the insert, the insert having an anterior stop with patellar relief according to example of the present application.

FIG. 7 shows another example of an insert 410 constructed in a manner similar to those previously described. The insert 410 can have a stop 412 positioned at or closely adjacent an anterior edge 414. The stop 412 can extend proximally from a proximal surface 416. As shown in the example of FIG. 7, the stop 412 can be configured with a patellar relief recess 418 therein. Such relief is typically provided by the bearing but the configuration of FIG. 7 can render such tibial relief on the bearing unnecessary.

FIG. 8 shows a system 500 according to an example of the present disclosure. The system 500 can include a tibial baseplate 502, a bearing 504 and an insert 506.

The insert 506 can be configured in the manner as previously described herein and can be configured to be disposable between the tibial baseplate 502 and the bearing 504. The tibial baseplate 502 can be configured to couple to a resected proximal surface of a tibia as previously described and illustrated in reference to FIG. 6, for example. The bearing 504 is generically illustrated in FIG. 8 and can comprise one of a plurality of bearings. Each of these bearings can have a recess 508 for receiving a post 510 of the insert 506 therein.

Each of the plurality of bearings can have a different construction and can be configured to replicate a bearing from a different knee system, for example. Thus, each of the plurality of bearings can be configured to articulate with a femoral implant of differing construction. According to some examples, the plurality of bearings 504 are configured to be substitutable for one another on the insert 506 without removal of the tibial baseplate 502 and the insert 506 from the knee joint of the patient.

Figure 10:
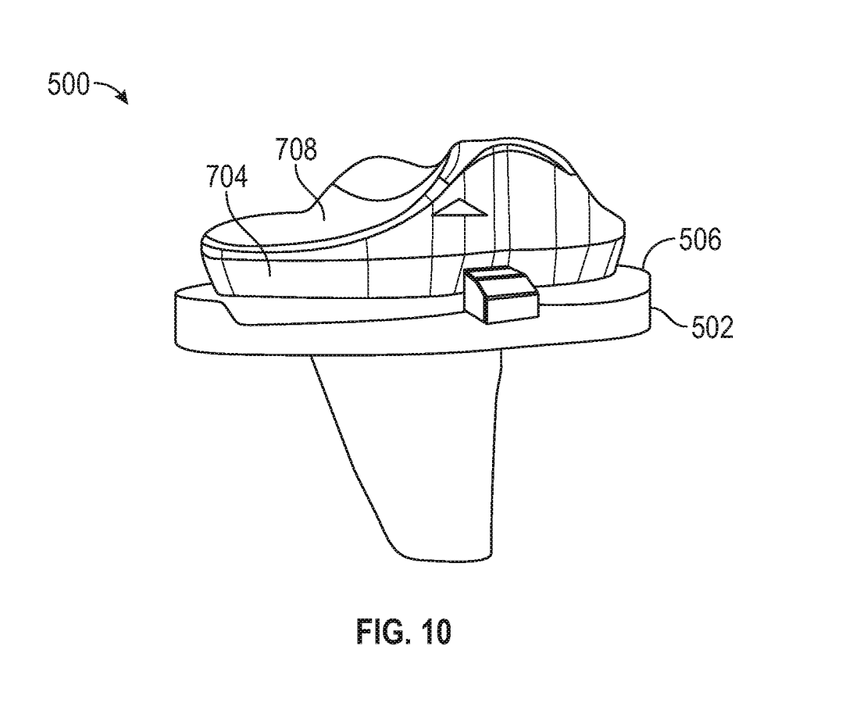
FIG. 10 is a perspective view of the system of FIG. 8 with a specific example of a bearing having a construction of that of a bearing from Zimmer Biomet's Vanguard® Tibial System according to another example of the present application.

FIGS. 9A-10 show various examples of the system 500 with different bearings used therewith. In FIGS. 9A and 9B, an insert 506 can have a construction similar to any one or any combination of the inserts previously described in reference to FIGS. 3A-8. More particularly, the insert 506 can be configured to couple to a tibial baseplate 502 that can be from Zimmer Biomet's Persona® Knee System.

FIG. 9A shows an exploded view of the system 500. FIG. 9B shows the system 500 with the tibial baseplate 502, the insert 506 and a bearing 604 assembled together. The insert 506 can also be disposable between the bearing 604 and the tibial baseplate 502. The bearing 604 can have a proximal surface 608 that has an identical shape to that of a bearing from Zimmer Biomet's Persona® Knee System. The bearing 604 can have a modified distal surface (e.g., no connection mechanisms) and can have a recess 622 (FIG. 9A) therein. The bearing 604 can be a posterior constrained design as shown in FIGS. 9A and 9B. However, according to other examples, the bearing can be at least one of a medial congruent design, an ultra-congruent design, the posterior constrained design and a posterior constrained revision design.

As the tibial baseplate 502 can be the tibial baseplate of Zimmer Biomet's Persona® Knee System, the tibial baseplate 502 can have a corresponding connection mechanism 610 that is designed to connect with the connection mechanism 32 previously described in reference to FIGS. 3A-3C. The connection mechanism 610 can include a double dovetail boss 612 on the tibial baseplate 502 (configured to cooperate with a corresponding notch on the insert 506), a peripheral rail 614 of the tibial baseplate 502 (configured to cooperate with a corresponding recessed portion of the insert 506) and can include other or different features according to other examples.

The insert 506 can be constructed as previously described, and can include a proximal surface 616, a post 618, and a distal surface 620. The proximal surface 616 can be configured to interface with the bearing 604. The post 618 can extend from the proximal surface 616 and can be configured to be received in the recess 622 (FIG. 9A) in the bearing 604. The bearing 604 can be configured to pivot about the post 618 to move relative to the proximal surface 616. The distal surface 620 can be spaced from the proximal surface 616, and can be configured to interface with the tibial baseplate 502. The distal surface 620 can be configured with a connection mechanism such as connection mechanism 32 (FIGS. 3B and 3C) to connect with the tibial baseplate 502.

FIG. 10 shows an alternative design for the system 500. In this example, the tibial baseplate 502 and the insert 506 design can remain the same (i.e. having a construction of Zimmer Biomet's Persona® Knee System). However, in the example of FIG. 10, a bearing 704 is used that is configured in the manner of a bearing used by Zimmer Biomet's Vanguard® ROCC Tibial System. More particularly, the bearing 704 has a proximal surface 708 that has an identical shape to that of one of the bearings from Zimmer Biomet's Vanguard® ROCC Tibial System and can be used with a femoral prosthesis from Zimmer Biomet's Vanguard® Femoral System. As previously discussed, the bearings (either 604 or 704) can be configured to be substitutable for one another on the insert 506 without removal of the tibial baseplate 502 and the insert 506 from the knee joint of the patient.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A tibial insert for replacement of a knee joint of a patient, the insert comprising:
   a proximal surface configured to interface with a bearing;
   a post extending from the proximal surface and configured to be received in a recess in the bearing, wherein the bearing is configured to pivot about the post to move relative to the proximal surface; and
   a distal surface spaced from the proximal surface and configured to interface with a tibial baseplate, wherein the distal surface is configured with a connection mechanism to connect with the tibial baseplate;
   wherein the insert has a differing thickness between the proximal surface and the distal surface as measured at one or both of a medial edge relative to a lateral edge and an anterior edge relative to a posterior edge.

2. The insert of claim 1, further comprising a stop extending from the proximal surface and configured to limit movement of the bearing relative to the insert about the post.

3. The insert of claim 2, wherein the stop is configured with a patellar relief recess therein.

4. The insert of claim 1, wherein the proximal surface is substantially planar.

5. The insert of claim 1, wherein the insert includes an internal lattice to reinforce the insert.

6. The insert of claim 1, wherein the connection mechanism comprises a dovetail configured to mate with a corresponding second dovetail provided by the tibial baseplate.

7. The insert of claim 1, further comprising a recess in the post and the post configured with a connection feature within the recess to facilitate lockdown of the bearing to the insert.

8. The insert of claim 1, wherein the bearing comprises one of a medial congruent design, an ultra-congruent design, a posterior constrained design and a posterior constrained revision design.

9. A system for replacement of a knee joint of a patient, the system comprising:
   a tibial baseplate configured to couple to a resected proximal surface of a tibia;
   a plurality of bearings each of the plurality of bearings have a different construction and are configured to simulate a bearing from a different knee system, and wherein each of the plurality of bearings are configured to articulate with a femoral implant of a different construction; and
   an insert disposable between the one or more bearings and the tibial baseplate, the insert comprising:
   a proximal surface configured to interface with the one or more bearings;
   a post extending from the proximal surface and configured to be received in a recess in each of the one or more bearings, wherein each of the one or more bearings is configured to pivot about the post to move relative to the proximal surface; and
   a distal surface spaced from the proximal surface and configured to interface with the tibial baseplate, wherein the distal surface is configured with a connection mechanism to connect with the tibial baseplate.

10. The system of claim 9, wherein the one or more bearings are configured to be substitutable for one another on the insert without removal of the tibial baseplate and the insert from the knee joint of the patient.

11. The system of claim 9, wherein the insert includes a stop extending from the proximal surface and configured to limit movement of the one or more bearings relative to the insert about the post.

12. The system of claim 11, wherein the stop is configured with a patellar relief recess therein.

13. The system of claim 9, wherein the proximal surface is substantially planar.

14. The system of claim 9, wherein the insert has a differing thickness between the proximal surface and the distal surface as measured at one or both of a medial edge relative to a lateral edge and an anterior edge relative to a posterior edge.

15. The system of claim 9, wherein the insert includes an internal lattice to reinforce the insert.

16. The system of claim 9, wherein the connection mechanism comprises a dovetail configured to mate with a corresponding second dovetail provided by the tibial baseplate.

17. The system of claim 9, wherein the one or more bearings comprises at least one of a medial congruent design, an ultra-congruent design, a posterior constrained design and a posterior constrained revision design.

18. A system for replacement of a knee joint of a patient, the system comprising:
   a tibial baseplate configured to couple to a resected proximal surface of a tibia;
   an insert configured to affix to the tibial baseplate, the insert having a proximal surface and a post extending from the proximal surface; and
   a bearing configured to receive the post therein, wherein the bearing is configured to pivot about the post to move relative to the proximal surface, wherein the bearing comprises a plurality of bearings each of the plurality of bearings have a different construction and are configured to simulate a bearing from a different knee system, and wherein each of the plurality of bearings are configured to articulate with a femoral implant of a different construction.

19. The system of claim 18, wherein the plurality of bearings are configured to be substitutable for one another on the insert without removal of the tibial baseplate and the insert from the knee joint of the patient.

* * * * *